US007910143B2

(12) United States Patent
Kvist et al.

(10) Patent No.: US 7,910,143 B2
(45) Date of Patent: Mar. 22, 2011

(54) SOLUBLE DIETARY FIBRE FROM OAT AND BARLEY GRAINS, METHOD FOR PRODUCING A FRACTION RICH IN B-GLUCAN AND USE OF THE FRACTION IN FOODS, PHARMACEUTICALS AND COSMETICS

(75) Inventors: Sten Kvist, Ödåkra (SE); John Mark Lawther, Roskilde (DK)

(73) Assignee: Biovelop International B.V., Amstelveen (NL)

( * ) Notice: Subject to any disclaimer, the term of this patent is extended or adjusted under 35 U.S.C. 154(b) by 1059 days.

(21) Appl. No.: 11/440,296

(22) Filed: May 24, 2006

(65) Prior Publication Data
US 2006/0280838 A1    Dec. 14, 2006

Related U.S. Application Data

(63) Continuation of application No. PCT/SE2004/001733, filed on Nov. 24, 2004.

(30) Foreign Application Priority Data

Nov. 24, 2003    (SE) .................................... 0303105

(51) Int. Cl.
*A23L 1/10* (2006.01)
*A23L 1/105* (2006.01)
(52) U.S. Cl. ................ 426/28; 426/18; 426/44; 426/49; 426/52; 426/478; 426/507
(58) Field of Classification Search .......................... None
See application file for complete search history.

(56) References Cited

U.S. PATENT DOCUMENTS

| 6,309,872 | B1 * | 10/2001 | Rey et al. ...................... 435/205 |
| 6,323,338 | B1 * | 11/2001 | Potter et al. .............. 536/123.12 |
| 6,426,201 | B1 * | 7/2002 | Morgan .......................... 435/99 |
| 6,592,914 | B1 | 7/2003 | Triantafyllou |
| 2002/0018830 | A1 * | 2/2002 | Whalen ........................... 426/28 |
| 2003/0153746 | A1 * | 8/2003 | Van Lengerich et al. ....................... 536/123.12 |

FOREIGN PATENT DOCUMENTS

CN    1324216 A    11/2001
(Continued)

OTHER PUBLICATIONS

WO/02/067698 Kvist et al. 2002 Process for Fractionation of Cereal Brans.*

(Continued)

*Primary Examiner* — Timothy M Speer
*Assistant Examiner* — Felicia C King
(74) *Attorney, Agent, or Firm* — Gauthier & Connors LLP

(57) ABSTRACT

The present invention relates to a process for the extraction of soluble dietary fiber from oat and barley grains using enzymatic hydrolysis treatment, wherein the grain is milled and any endosperm depleted fractions thereof being rich in B-glucans are recombined, without further heat treatment, dispersed in water and then subjected to sequential enzymatic treatment with starch degrading enzymes, followed by an optional step of enzyme inactivation by wet heat treatment, and a subsequent step wherein the hydrolysate mixture is spontaneously or centrifugally separated into at least 3 distinct fractions: a first fraction, which comprises the soluble dietary fiber complex, containing more than 20% B-glucan on a dry matter basis, a second aqueous fraction, and a third fraction comprising most of the protein and oil together with the insoluble fibrous material from the milled grain.

11 Claims, 2 Drawing Sheets

FOREIGN PATENT DOCUMENTS

WO     WO 00/24270     5/2000
WO     WO 02/065855     8/2002

OTHER PUBLICATIONS

Guan Xiao et al., ; "Extract of Beta-Glucan From Oat Bran and Determination of its Molecular Weight Distribution"; Food Science, 2003; vol. 24. No. 7, pp. 40-43.

Shen Ruiling et al.,; "Extraction and Purification of Beta-Glucans In Grains"; Cereal & Feed Industry; 2003, No. 7, pp. 42-43.

Office Action in corresponding Chinese Patent Application No. 2004800395049, with English translation.

Zhang et al., "Effects of Oat Grain Hydrothermal Treatments on Wheat-Oat flour Dough Properties and Breadbaking Quality" Cereal Chem. 75(5):1998, pp. 602-605.

\* cited by examiner

SOLUBLE DIETARY FIBRE FROM OAT AND BARLEY GRAINS, METHOD FOR PRODUCING A FRACTION RICH IN B-GLUCAN AND USE OF THE FRACTION IN FOODS, PHARMACEUTICALS AND COSMETICS

This application is a continuation of PCT Application No. PCT/SE2004/001733 filed Nov. 24, 2004 which claims priority to Swedish Application No. 0303105-1, filed on Nov. 24, 2003.

TECHNICAL FIELD

The present invention relates to a process for the cost-effective extraction of high molecular weight soluble dietary fibres and functional non-starch polysaccharides, from oat and barley grains and the downstream enrichment and utilization of these materials. A novel methodology to produce β-glucans of high and medium molecular weight, in a controlled, cost effective manner, is described.

BACKGROUND OF THE INVENTION

There are acknowledged health and nutritional benefits for humans in increasing the daily intake of soluble dietary fibres from oat and barley grains. In particular, the β-glucan component of these cereals has been related and directly linked to a number of beneficial effects, for example the demonstrated reduction of serum cholesterol levels, alongside improvements in HDL/LDL ratios in the blood, an effect strongly correlated with improved cardiovascular health in humans [Bell et al, Critical Reviews In Food Science and Nutrition, Vol 39, 2, 1999]. Additionally, highly viscous (and usually high molecular weight) non-starch polysaccharides present in whole cereal grains, may be implicated in mechanisms regulating blood glucose, with an implied beneficial effect in long term prevention of type 2 diabetes [Foster-Powell and Brand Miller, Am J. Clin. Nutr., 62, 871S-893S, 1995]. Of further significance, the soluble dietary fibres present in oat and barley are not digested in the human intestine and therefore pass through to the colon where they are available for microbial fermentation and as such are effective prebiotic materials.

Furthermore, the soluble β-glucans from oat and barley are very interesting as functional ingredients in foods as they exhibit gelling behaviour, stabilising properties, water binding and impart good mouth feel to products. High molecular weight β-glucans have potential as viscosity modifiers, colloidal stabilisers, texturisers etc in foodstuffs.

For many of the nutraceutical and Functional applications, it is crucial to maintain high molecular weights in the β-glucan component of the soluble fibre and to isolate the soluble fibre cost-effectively with a reasonably high concentration of β-glucan in the isolate. This "double challenge" is addressed in the present invention. Additionally, isolation of a reasonably clean fraction of soluble dietary fibre containing high molecular weight β-glucan at appreciable concentrations facilitates the cost-effective further processing of the material to yield preparations of very high β-glucan concentrations at high molecular weight, and to adjust molecular weight of the materials in a controlled manner to "tailor" final product properties. This issue is also addressed in the present invention. Finally, for soluble dietary fibres From oat and barley to impact significantly in the food markets, a process for their production must be cost effective and be capable of delivering materials at reasonable costs already accepted for food ingredients of various classes. The present invention also facilitates this.

Prior to the present invention, there exists no cost-effective process capable of, at the industrial scale, producing high molecular weight, concentrated preparations of soluble dietary fibre from oat and barley, which can be utilised directly as food ingredients. There is additionally no process, which can deliver β-glucan products of pre-determined molecular weight profiles, necessary to ensure correct function of the products in targeted end applications.

For example, inglett in two patent applications (U.S. Pat. No. 4,996,063 and WO 92/10106) describes methods to produce water-soluble dietary fibre compositions from milled, heat-treated oat flours and milled barley flours, via treatment with α-amylase enzymes to degrade starch components and subsequent centrifugation to remove insoluble materials from the hydrolysate mixture. The products are relatively low in soluble dietary fibre content, with no reference to the molecular weight of the β-glucan components. Only one enzyme type is utilised in the processes described. There is no description of a method to further enrich the β-glucan content of the material, or the separation of a distinct layer rich in high molecular weight β-glucan.

Lennart et al (U.S. Pat No. 5,686,123) inform on methods to produce soluble cereal suspensions from oat. The basis of the invention is treatment of previously heat-treated ground oat, with β-amylase class of enzyme, whilst slurried in water. A second α-amylase stage may be optionally included to further breakdown starch. No separation of a soluble dietary fibre rich component is described in the invention. The product slurry contains most of the protein and oil present in the raw material.

Triantafyllon, in WO 00/24270 describes a method to produce β-glucan soluble dietary fibre from heat-treated oat flour, using β-amylase enzyme to hydrolyse starch to lower molecular weight fragments, optionally including α-amylase and/or protease in a second stage hydrolysis, after which solids are centrifuged off, leaving a single soluble phase containing around up to 2% β-glucan before drying. There is no description or suggestion of the segregation of a fraction rich in soluble dietary fibre in this process, distinct from an aqueous syrup layer, and no product that can have a particularly high content of β-glucan is produced via the direct drying of the separated supernatant. The lack of a distinct separate viscous top layer on top of the bulk aqueous layer suggests there has been some degradation of β-glucans into smaller molecular weight fractions.

Indeed, most processes claiming to produce compositions containing high concentrations of soluble dietary fibres from oat and barley grain are based not on enzymatic extraction, but rather on alkaline extraction either from milled whole grain or a sleved fraction (Fisher et al, U.S. Pat No. 6,323, 338), or even hot water extraction, which yields lower molecular weight soluble β-glucans (Roxdale Foods Ltd and Morgan; WO 02/02645 A1).

A precise methodology has now been discovered that addresses and solves the problems outlined above. The invention allows the cost-effective production of oat and barley soluble dietary fibre preparations containing β-glucans of high molecular weight, in concentrations of typically 20%-30%. The fraction containing the high molecular weight soluble dietary fibre component (20%-30% of dry matter) separates as a distinct viscous top layer during the process, above another distinct aqueous layer containing water soluble components. The fraction is relatively free of proteins and oils normally encountered during the processes described above.

The clean fraction can then be separated very cost effectively from the other components and dries directly as a soluble white powder with negligible cereal taste. This of course greatly facilitates the further processing of this fraction containing the soluble dietary fibres with these characteristics and in these proportions, so that further enrichment (up to more than 60% β-glucan on a dry weight basis) becomes commercially and technically feasible. This is a major step forward in oat and barley processing.

SUMMARY OF THE PRESENT INVENTION

The main objectives of the present invention are to:
1. Attain an efficient cost effective industrial process to extract and yield, from oat and barley grains, high molecular weight (>1,300,000 Daltons) and medium molecular weight (>800,000 Daltons) soluble dietary fibre complexes containing β-glucan components, and optionally combinations of the following: arabinoxylan components, starch and/or starch fragments such as dextrins, sugars including glucose, and relatively low levels of contaminant oil (<2.5%) and protein (<7%). The β-glucan component of the extract is at least 20% on a dry matter basis. The molecular weight pertains to the demonstrably β-glucan portion of the complex. Under certain circumstances it may be desirable to obtain a β-glucan fraction having a smaller molecular weight such as above 400,000 Daltons.
2. Ensure that the fraction rich in high molecular weight soluble dietary fibre separates from other soluble and water-suspendable components, and from insoluble materials, as a distinct fraction, low in contaminant protein (<7%) and oil (<2.5%).
3. Attain an efficient cost effective process to upgrade the soluble dietary fibre rich fraction as obtained in 1. above, and to tailor properties such as molecular weight and structure, β-glucan content, functionality, solubility and hydration properties.
4. Attain an efficient cost effective industrial process to extract and yield physiologically active β-glucan containing materials useful in blood glucose modulation, serum cholesterol control and other nutraceutical applications.
5. Combine the use of dry milling, and dry fractionation of the milled grain, with the use of sequential enzymatic treatment, optionally combined with wet-milling, to allow efficient extraction of soluble dietary fibre complexes.
6. To maximise the amount of high molecular weight soluble dietary fibre in the (top layer) fraction separating after the enzymatic hydrolysis stages of the process.

It has been discovered that to produce, cost-effectively, material containing relatively high concentrations of soluble, high molecular weight β-glucans, it is advantageous to:
   i. Mill dehulled oat or barley to remove excess starchy endosperm material, and to retain around 50% of the milled grain, which is the coarser fraction.
   ii. Not heat-treat the milled fractions, which is novel for oat in that it is common practice to heat treat milled oats.
   iii. Suspend the milled fractions in water, and treat in a precise sequence firstly with α-amylase enzyme and then with either amyloglucosidase type of enzyme and/or a pullulanase enzyme in a distinct second stage. The mixture can optionally be passed through a wet mill during enzyme treatment.
   iv. Deactivate the enzymes by heat treatment and allow the hydrolysate mix to settle.

This sequence crucially facilitates the separation of a distinct fraction such as a settling top layer, in the hydrolysate suspension, which lies above an aqueous layer, with a further distinct bottom layer containing proteins and oils along with the insoluble fibrous portion of the milled grain. The top layer is particularly rich in high molecular weight soluble dietary fibre, mainly β-glucan with some arabinoxylan, alongside maltodextrins and some glucose sugar. This represents a clean separation of a native β-glucan complex from the other grain components, in that it is believed that the β-glucan component is close to its original form in the grain. In order for the β-glucans not to become degraded during the enzymatic process, it is essential to start with milled factions of oats that have not been heat-treated and to utilise an amyloglucosidase enzyme preparation that has been cleaned of β-glucanase side activities. Maintaining the intact β-glucan structure is a crucial factor in the formation of the distinct top layer, as the separate top layer is not formed if the β-glucans are degraded.

This separation is spontaneous in that this soluble dietary fibre rich component separates into a distinct top-layer if the hydrolysate suspension is left without agitation or stirring after completion of the enzymatic stages. Of course, centrifugation accelerates the formation of this top layer and the use of a 3-phase decanter allows efficient separation of this top-layer from the remainder of the hydrolysate liquor.

When separated, the top-layer contains normally 20 to 30% (on a dry matter basis), more normally 24%-27%, of high molecular weight β-glucan, with a low amount of contaminating proteins and oils. The layer is readily freeze dried or spray dried to a white—cream coloured powder.

Of course the recovery of such a β-glucan rich fraction using such cost-effective technology makes it economically and technically worthwhile to further upgrade the material, to either increase the β-glucan content relative to maltodextrins, or to modulate the β-glucan molecular weight in a controlled manner, or both, prior to final drying of the fraction. This can be achieved in two main ways, or by combined application of the two methodologies:

i. Treatment of the separated top layer with a pure amyloglucosidase (AMG) enzyme, or using a commercial amyloglucosidase enzyme preparation that has been cleaned of β-glucanase side activities in a two step procedure using anion exchange, followed by hydrophobic interaction chromatography, the major protein band eluting from the hydrophobic interaction chromatography stage being utilised as the cleaned enzyme. The AMG, free of β-glucanase side activities, substantially further degrades dextrins and maltodextrins to low molecular weight oligomers and glucose, whilst leaving the soluble dietary fibre components untransformed/undegraded, facilitating easy separation by ultra-filtration or precipitation into a mix of 50% ethanol/50% water, wherein the sugars remain dissolved in the liquid phase and the precipitated, polymeric carbohydrates can be removed by centrifugation, prior to drying. Using such a method it is possible to produce a material containing up to 70% β-glucan, on a dry weight basis.
   ii. Treatment of the separated top layer with one of, or a combination of, the following types of enzymes: Lichenase, xylanase, cellulase. In such a way, the molecular weight of the β-glucan soluble fibre complex can be reduced in a controlled manner, yielding products of predictable properties.
   iii. Combinations of i. and ii. above.

DETAILED DESCRIPTION OF THE PRESENT INVENTION

Figure 1:
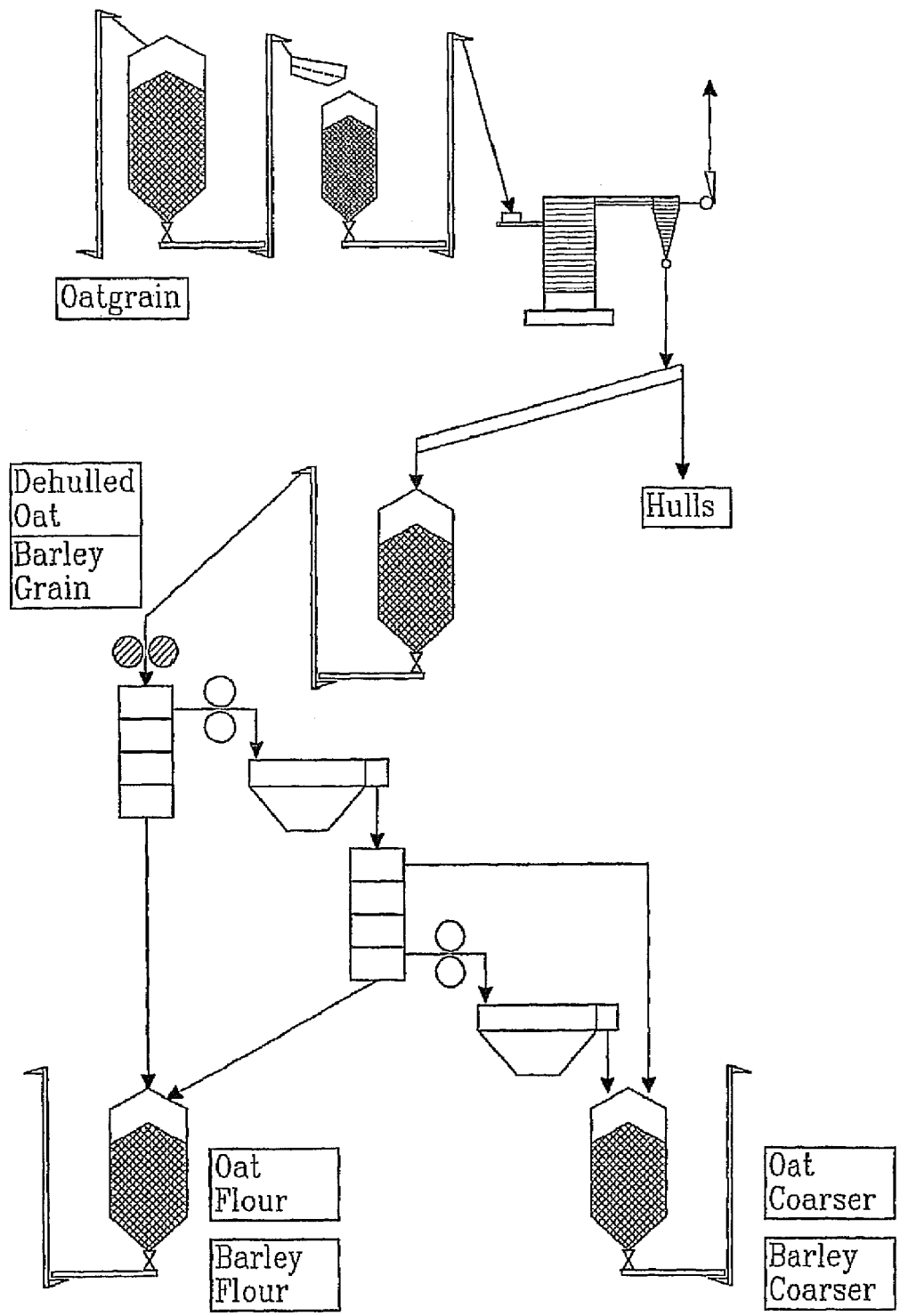
FIGS. 1 and 2 show a schematic overview of the set-up necessary for an industrial process wherein the set-up comprises two parts, viz. a dry process part and a wet process part.

According to the present invention there is provided an efficient, cost effective industrial process for the extraction of a valuable fraction from milled oat and barley grain, which is rich in soluble dietary fibre but relatively free of contaminant proteins and oils.

The present invention is characterized in that previously non-heat treated de-hulled oat and/or barley grain is first dry milled to an endosperm-starch rich flour fraction and a coarser endosperm-reduced fraction. The endosperm-reduced fraction comprises between 45% and 55% of the milled grain and is then further utilised without any further heat treatment, which is conventionally applied during oat processing and milling. The milled grain is added to water and treated sequentially with a starch degrading α-amylase enzyme, followed by a second hydrolysis step using an enzyme, or combination of enzymes, from the group amyloglucosidases and pullulanases. The enzyme treatments are optionally performed in combination with aqueous wet-milling. A further step is enzyme inactivation by wet heat treatment, followed by the spontaneous or centrifugal separation of the hydrolysate mix into a top-layer rich in soluble dietary fibre, mainly β-glucans, an aqueous layer and a lower layer containing proteins, oils and the insoluble fibrous portion of the grain.

In particular the present invention relates to a process for the extraction of soluble dietary fibre complex from oat and barley grains using a enzymatic hydrolysis treatment, which is characterized in that the non-heat treated grain is milled and any endosperm depleted fractions thereof being rich in β-glucans are recombined without any further heat treatment, dispersed in water and then subjected to enzymatic treatment with starch degrading enzymes being free of β-glucanase, followed by an optional step of enzyme inactivation by wet heat treatment, whereby the hydrolysate mixture forming spontaneously at least one viscous, aqueous top layer upon a second aqueous layer, is subjected to a separation process to isolate said at least one viscous, aqueous top layer comprising the soluble dietary fibre complex, containing more than 20% β-glucan on a dry matter basis.

In accordance with a preferred embodiment of the invention a second aqueous fraction layer substantially free of β-glucans, and at least a third fraction layer comprising most of the protein and oil together with the insoluble fibrous material from the milled grain are isolated.

In accordance with a further preferred embodiment of the invention the isolated β-glucan has a molecular weight of at least 400,000 Daltons.

In accordance with another preferred embodiment of the invention the isolated β-glucan has a molecular weight of at least 800,000 Daltons.

In accordance with a preferred embodiment of the invention the isolated β-glucan has a molecular weight of at least 1,300,000 Daltons.

The distinct top layer can be removed in a 3-phase decanter or other suitable device, yielding a soluble fraction containing at least 20% (on a dry matter basis) β-glucan soluble dietary fibre which is of high molecular weight (>1,300,000 Daltons) to medium molecular weight (>800,000 Daltons), along with maltodextrins, arabinoxylans, sugars and relatively low amounts of protein (<7%) and oils (<2.5%).

The separated top layer rich in soluble dietary fibre can then be further treated prior to drying using further enzymatic hydrolysis by way of post-treatment using enzymes of the following types, or combinations of those enzymes: Lichenase, cellulase, xylanase. This allows the reduction of molecular weight of the β-glucan component of the liquor, and/or the fine tuning of its properties, in a controlled manner.

In a preferred embodiment, the raw material is de-hulled oat, or barley grain, which is dry-milled to remove excess starchy endosperm. Between 45%-55% of the milled grain is retained and used in the wet-process, comprising the coarser fraction. This is not heat treated in the dry state prior to utilisation.

In a preferred embodiment the milled grain fractions are added to water and then treated with starch-degrading enzymes in a specific sequence, a first stage involving treatment with an enzyme of the amylase type, with optionally concomitant wet-milling, followed by a second stage using an enzyme of the amyloglucosidase and/or pullulanase groups with optionally concomitant wet-milling, whereby the time is up to 40 minutes and treatment at temperatures of 55° C. or greater for the second stage.

In a preferred embodiment the milled cereal grain fractions are added to water and then treated with starch degrading enzymes in a sequence utilising first α-amylase and then amyloglucosidase enzyme, in which the amyloglucosidase enzyme is substantially cleaned of β-glucanase side activities prior to use, in a two step procedure using anion exchange followed by hydrophobic interaction chromatography, the major protein band eluting from the hydrophobic interaction chromatography column being utilised as the cleaned enzyme.

In a preferred embodiment, the hydrolysate spontaneously separates, or is optionally separated centrifugally into 3 distinct layers, a top-layer which is rich in soluble dietary fibres, particularly β-glucans, but containing little oil (<2.5%) or protein (<7%), a middle aqueous layer, and a lower phase containing most of the protein, oil and insoluble fibrous material from the milled grain.

In a preferred embodiment, the top-layer in which the soluble dietary fibres are concentrated is subjected to a further treatment in the wet state using one or a combination of enzymes of the type: Lichenase, cellulase, xylanase. After treatment, the material is heated to inactivate the enzymes and then either freeze dried or spray dried to a powder.

In a preferred embodiment, the separated top-layer rich in soluble dietary fibre is further treated in the wet state, after optionally further diluting with water, with amyloglucosidase enzyme, in which the amyloglucosidase enzyme is substantially cleaned of β-glucanase side activities prior to use, in a two step procedure using anion exchange followed by hydrophobic interaction chromatography, isolating the major protein band eluting from the hydrophobic interaction chromatography column and utilising said major protein band as an AMG freed of β-glucanase side activity as the cleaned enzyme, isolating the fraction rich in β-glucan and optionally purifying the same from any content of maltose and/or glucose; i.e. by use of ultrafiltration and/or precipitation.

The isolated β-glucans can be used in a dry state as well as in a wet state.

In a preferred embodiment, the said fraction contains at least 20% and up to 40% β-glucan soluble dietary fibre, not more than 10% protein, preferably less-than 7% protein, more preferably less than 5% protein, and less than 2.5% oil preferably less than 2.0%, more preferably less than 1.5%, still more preferably less than 1.0%, on a dry matter basis. The β-glucan component has a molecular weight of at least 800,000 Daltons.

In a preferred embodiment, the said fraction contains at least 20% and up to 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0% on a dry matter basis. The β-glucan component has a molecular weight of at least 1,300,000 Daltons.

In a preferred embodiment, the said fraction contains at least 40% β-glucan soluble dietary fibre, not more than 10% protein, preferably less than 7% protein, more preferably less than 5% protein, and less than 2.5% oil preferably less than 2.0%, more preferably less than 1.5%, still more preferably less than 1.0%, on a dry matter basis. The β-glucan component has a molecular weight of at least 800,000 Daltons.

In a preferred embodiment, the said fraction contains at least 40% β-glucan soluble dietary fibre, not more than 10% protein, preferably less than 7% protein, more preferably less than 5% protein, and less than 2.5% oil preferably less than 2.0%, more preferably less than 1.5%, still more preferably less than 1.0%, on a dry matter basis. The β-glucan component has a molecular weight of at least 1,300,000 Daltons.

In a preferred embodiment, each of the fractions rich in soluble dietary fibre described above is used as an additive for food, feedstuffs, pharmaceuticals, and cosmetics.

In a preferred embodiment, the said fraction which contains at least 20% and up to 40% β-glucan soluble dietary fibre, not more than 10% protein, preferably less than 7% protein, more preferably less than 5% protein, and less than 2.5% oil preferably less than 2.0%, more preferably less than 1.5%, still more preferably less than 1.0%, and that has a β-glucan component with a molecular weight of at least 800,000 Daltons, is used as an additive for fruit juice and/or water based drinks.

In a preferred embodiment, the said fraction which contains at least 20% and up to 40% β-glucan soluble dietary fibre, not more than 10% protein, preferably less than 7% protein, more preferably less than 5% protein, and less than 2.5% oil preferably less than 2.0%, more preferably less than 1.5%, still more preferably less than 1.0%, and that has a β-glucan component with a molecular weight of at least 1,300,000 Daltons, is used as an additive for fruit juice and/or water based drinks.

In a preferred embodiment, the said fraction which contains at least 40% β-glucan soluble dietary fibre, not more than 10% protein, preferably less than 7% protein, more preferably less than 5% protein, and less than 2.5% oil preferably less than 2.0%, more preferably less than 1.5%, still more preferably less than 1.0%, and that has a β-glucan component with a molecular weight of at least 800,000 Daltons, is used as an additive for fruit juice and/or water based drinks.

In a preferred embodiment, the said fraction which contains at least 40% β-glucan soluble dietary fibre, not more than 10% protein, preferably less than 7% protein, more preferably less than 5% protein, and less than 2.5% oil preferably less than 2.0%, more preferably less than 1.5%, still more preferably less than 1.0%, and that has a β-glucan component with a molecular weight of at least 1,300,000 Daltons, is used as an additive for fruit juice and/or water based drinks.

A further aspect of the invention relates to the use of the said fraction containing at least 20% and up to 40% β-glucan soluble dietary fibre, not more than 10% protein, preferably less than 7% protein, more preferably less than 5% protein, and less than 2.5% oil preferably less than 2.0%, more preferably less than 1.5%, still more preferably less than 1.0%, on a dry matter basis, and with the β-glucan component having a molecular weight of at least 800,000 Daltons, as an additive for yoghurts, milk-based drinks and other liquid fermented milk preparations.

A further aspect of the invention relates to the use of the said fraction containing at least 20% and up to 40% β-Glucan soluble dietary fibre, not more than 10% protein, preferably less than 7% protein, more preferably less than 5% protein, and less than 2.5% oil preferably less than 2.0%, more preferably less than 1.5%, still more preferably less than 1.0%, on a dry matter basis, and with the β-glucan component having a molecular weight of at least 1,300,000 Daltons, as an additive for yoghurts, milk-based drinks and other liquid fermented milk preparations.

A further aspect of the invention relates to the use of the said fraction containing at least 40% β-glucan soluble dietary fibre, not more than 10% protein, preferably less than 7% protein, more preferably less than 5% protein, and less than 2.5% oil preferably less than 2.0%, more preferably less than 1.5%, still more preferably less than 1.0%, on a dry matter basis, and with the β-glucan component having a molecular weight of at least 800,000 Daltons, as an additive for yoghurts, milk-based drinks and other liquid fermented milk preparations.

A further aspect of the invention relates to the use of the said fraction containing at least 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of not less than 1,300,000 Daltons, as an additive for yoghurts, milk-based drinks and other liquid fermented milk preparations.

A further aspect of the invention relates to the use of the said fraction containing at least 20% and up to 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 800,000 Daltons, as an additive for ice creams and frozen desserts.

A further aspect of the invention relates to the use of the said fraction containing at least 20% and up to 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 1,300,000 Daltons, as an additive for ice creams and frozen desserts.

A further aspect of the invention relates to the use of the said fraction containing at least 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 800,000 Daltons, as an additive for ice creams and frozen desserts.

A further aspect of the invention relates to the use of the said fraction containing at least 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 1,300,000 Daltons, as an additive for ice creams and frozen desserts.

A further aspect of the invention relates to the use of the said fraction containing at least 20% and up to 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 800,000 Daltons, as an additive for butter based spreads, spreads and margarines, functioning as a blood cholesterol modulating, and /or blood glucose modulating, and/or prebiotic agent.

A further aspect of the invention relates to the use of the said fraction containing at least 20% and up to 40% β-glucan soluble dietary fibre, not more than 10% protein, preferably less than 7% protein, more preferably less than 5% protein, and less than 2.5% oil, preferably less than 2.01%, more preferably less than 1.5%, still more preferably less than 1.0%, on a dry matter basis, and with the β-glucan component having a molecular weight of at least 1,300,000 Daltons, as an additive for butter based spreads, spreads and margarines, functioning as a blood cholesterol modulating, and/or blood glucose modulating, and/or prebiotic agent.

A further aspect of the invention relates to the use of the said fraction containing at least 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 800,000 Daltons, as an additive for butter based spreads, spreads and margarines, functioning as a blood cholesterol modulating, and /or blood glucose modulating, and/or prebiotic agent.

A further aspect of the invention relates to the use of the said fraction containing at least 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 1,300,000 Daltons, as an additive for butter based spreads, spreads and margarines, functioning as a blood cholesterol modulating, and/or blood glucose modulating, and/or prebiotic agent.

A further aspect of the invention relates to the use of the said fraction containing at least 20% and up to 40% β-glucan soluble dietary fibre, not more than. 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 800,000 Daltons, as an additive for cheeses.

A further aspect of the invention relates to the use of the said fraction containing at least 20% and up to 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 1,300,000 Daltons, as an additive for cheeses.

A further aspect of the invention relates to the use of the said fraction containing at least 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 800,000 Daltons, as an additive for cheeses.

A further aspect of the invention relates to the use of the said fraction containing at least 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 1,300,000 Daltons, as an additive for cheeses.

A yet further aspect of the invention relates to the use of the said fraction containing at least 20% and up to 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 800,000 Daltons, as an additive for processed meat products such as burgers, meatballs, sausages, salamis, pates and pastes, as a texturising and/or moisture retaining agent and/or prebiotic agent and/or blood glucose modulating agent.

A yet further aspect of the invention relates to the use of the said fraction containing at least 20% and up to 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 1,300,000 Daltons, as an additive for processed meat products such as burgers, meatballs, sausages, salamis, pates and pastes, as a texturising and/or moisture retaining agent and/or prebiotic agent and/or blood glucose modulating agent.

A yet further aspect of the invention relates to the use of the said fraction containing at least 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 800,000 Daltons, as an additive for processed meat products such as burgers, meatballs, sausages, salamis, pates and pastes, as a texturising and/or moisture retaining agent and/or prebiotic agent and/or blood glucose modulating agent.

A yet further aspect of the invention relates to the use of the said fraction containing at least 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 1,300,000 Daltons, as an additive for processed meat products such as burgers, meatballs, sausages, salamis, pates and pastes, as a texturising and/or moisture retaining agent and/or prebiotic agent and/or blood glucose modulating agent.

A yet further aspect of the invention relates to the use of the said fraction containing at least 20% and up to 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 800,000 Daltons, as an additive for baked goods such as breads and cakes as a texturising and/or moisture retaining agent and/or anti-staling agent and/or blood glucose modulating agent and/or a serum cholesterol modulating agent and/or a prebiotic agent.

A yet further aspect of the invention relates to the use of the said fraction containing at least 20% and up to 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of not less than 1,300,000 Daltons, as an additive for baked goods such as breads and cakes as a texturising and/or moisture retaining agent and/or anti-staling agent and/or a blood glucose modulating agent and/or a serum cholesterol modulating agent and/or prebiotic agent.

A yet further aspect of the invention relates to the use of the said fraction containing at least 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 800,000 Daltons, as an additive for baked goods such as breads and cakes as a texturising and/or moisture retaining agent and/or anti-staling agent and/or blood glucose modulating agent and/or a serum cholesterol modulating agent and/or a prebiotic agent.

A yet further aspect of the invention relates to the use of the said fraction containing at least 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of not less than 1,300,000 Daltons, as an additive for baked goods such as breads and cakes as a texturising and/or moisture retaining agent and/or anti-staling agent and/or a blood glucose modulating agent and/or a serum cholesterol modulating agent and/or prebiotic agent.

A yet further aspect of the invention relates to the use of the said fraction containing at least 20% and up to 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 800,000 Daltons, as a functional additive for cosmetic products such as skin ointments, creams, emollients.

A yet further aspect of the invention relates to the use of the said fraction containing at least 20% and up to 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 1,300,000 Daltons, as a functional additive for cosmetic products such as skin ointments, creams, emollients.

A yet further aspect of the invention relates to the use of the said fraction containing at least 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 800,000 Daltons, as a functional additive for cosmetic products such as skin ointments, creams, emollients.

A yet further aspect of the invention relates to the use of the said fraction containing at least 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 1,300,000 Daltons, as a functional additive for cosmetic products such as skin ointments, creams, emollients.

A yet further aspect of the invention relates to the use of the said fraction containing at least 20% and up to 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 800,000 Daltons, as a component of a pill or capsule formulation as a prebiotic and/or a blood glucose modulating agent and/or a serum cholesterol modulating agent.

A yet further aspect of the invention relates to the use of the said fraction containing at least 20% and up to 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 1,300,000 Daltons, a component of a pill or capsule formulation as a prebiotic and/or a blood glucose modulating agent and/or a serum cholesterol modulating agent.

A yet further aspect of the invention relates to the use of the said fraction containing at least 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 800,000 Daltons, as a component of a pill or capsule formulation as a prebiotic and/or a blood glucose modulating agent and/or a serum cholesterol modulating agent.

A yet further aspect of the invention relates to the use of the said fraction containing at least 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and, with the β-glucan component having a molecular weight of at least 1,300,000 Daltons, a component of a pill or capsule formulation as a prebiotic and/or a blood glucose modulating agent and/or a serum cholesterol modulating agent.

A yet further aspect of the invention relates to the use of the said fraction containing at least 20% and up to 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 800,000 Daltons, as a component in slow and/or controlled released devices for pharmaceutical applications.

A yet further aspect of the invention relates to the use of the said fraction containing at least 20% and up to 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 1,300,000 Daltons, as a component in slow and/or controlled released devices for pharmaceutical applications.

A yet further aspect of the invention relates to the use of the said fraction containing at least 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 800,000 Daltons, as a component in slow and/or controlled released devices for pharmaceutical applications.

A yet further aspect of the invention relates to the use of the said fraction containing at least 40% β-glucan soluble dietary fibre, not more than 10% protein, preferably less than 7% protein, more preferably less than 5% protein, and less than 2.5% oil, preferably less than 2.0%, more preferably less than 1.5%, still more preferably less than 1.0%, on a dry matter basis, and with the β-glucan component having a molecular weight of at least 1,300,000 Daltons, as a component in slow and/or controlled released devices for pharmaceutical applications.

DESCRIPTION OF THE PREFERRED EMBODIMENTS

Example 1

Raw material was prepared as follows: Oat grain was first de-hulled and the de-hulled grains were dry milled and 50% by weight of the grain was retained as a coarser fraction. 575 g of this material was suspended in 4 liters of water at a temperature of 95° C., in a 5 liter reaction vessel fitted with a mechanical stirrer. α-amylase enzyme (35 units) was added to the suspension and the mixture was incubated, with stirring and intermittent wet-milling, for 1 hour After this time, the pH was dropped to 4.5, the temperature lowered to 75° C. and amyloglucosidase (AMG) enzyme was added (35 units), the mixture being incubated for 15 minutes with stirring. Enzymes were then completely de-activated by heating of the suspension in an autoclave at 140° C. for some minutes.

The resulting suspension was then centrifuged, producing four distinct layers which were separated and collected; a viscous top layer rich in soluble dietary fibre, particularly β-glucan, an aqueous layer comprising dextrins and sugars, in particular maltose and maltotriose, <1% fat, and <3% proteins, a protein-oil rich layer and a bottom layer containing the insoluble fibrous part of the milled oat. The top-layer and protein-oil layers were freeze dried prior to analysis. The fibrous layer was dried at 60° C. in an oven.

The yields of top layer, protein-oil fraction and the fibre fraction were 15%, 15% and 20.0% respectively (on a dry matter basis). The remainder was mostly soluble sugars and dextrins.

The top layer was further analysed for β-glucan content, residual protein and fat etc with the following results:
β-glucan: 24.5%, protein: 5.0%, fat: 1.8%

A sub-sample of the dried top-layer material was then dissolved in 0.05 M sodium chloride solution to a concentration of 0.1% and the molecular weight of the polymeric components was estimated using HPSEC (High Performance Size Exclusion Chromatography) on a combined Ultragel GPC column system, using pullulans as Standards. The mean peak molecular weight of the β-glucan component of the material was estimated at >1.3 million Daltons, against the pullulan standard calibration used.

Example 2

Barley grain was dry milled to remove excess endosperm material and 50% of the milled grain, representing the coarser fraction, was utilized as the raw material for the trial.

575 g of this material was suspended in 4 liters of water at a temperature of 95° C., in a 5 liter reaction vessel fitted with a mechanical stirrer. α-amylase enzyme (35 units) was added to the suspension and the mixture was incubated, with stirring and intermittent wet-milling, for 1 hour. After this time, the pH was dropped to 4.5, the temperature lowered to 75° C. and amyloglucosidase (AMG) enzyme was added (35 units), the mixture being incubated for 15 minutes with stirring. Enzymes were then completely de-activated by heating of the suspension in an autoclave at 140° C. for some minutes.

The resulting suspension was then centrifuged, producing four distinct layers which were separated and collected; a viscous top layer rich in soluble dietary fibre, particularly β-glucan, an aqueous layer, a protein-oil rich layer and a bottom layer containing the insoluble fibrous part of the milled oat. The top-layer and protein-oil layers were freeze dried prior to analysis. The fibrous layer was dried at 60° C. in an oven.

The yields of top layer, protein-oil fraction and the fibre fraction were 15%, 15.4% and 21.4% respectively.

The top layer was further analysed for β-glucan content, residual protein and etc with the following results:
β-glucan: 24.7%, protein: 5.1%, fat: 0.4%

A sub-sample of the dried top-layer material was then dissolved in 0.05 M sodium chloride solution to a concentration of 0.1% and the molecular weight of the polymeric components was estimated using HPSEC on a combined Ultragel GPC column system, using pullulans as Standards. The mean peak molecular weight of the β-glucan component of the material was estimated at >1.3 million Daltons.

Example 3

The same raw material as prepared in example 1 was used in this trial. 150 Kg of this material was added to 1050 liters of water at 95° C. in a 2,000 liter tank fitted with mechanical stirring.

α-amylase enzyme (9100 units) was added to the suspension and the mixture was incubated, with stirring and intermittent wet-milling, for 1 hour. After this time, the pH was dropped to 4.5 using 84% orthophosphoric acid, the temperature lowered to 75° C. and amyloglucosidase (AMG) enzyme was added (9000 units), the mixture being incubated for 15 minutes with stirring. Enzymes were then completely de-activated by heating the resultant suspension by passing through a tubular heat exchanger at 140° C. The partially cooled hydrolysate suspension was then pumped into a 3-phase decantor and three fractions were obtained: a viscous top-layer rich in soluble dietary fibres, an aqueous fraction and a fraction containing most of the protein, fat and insoluble fibre from the milled oat grain.

The yields of the top layer, and the protein-oil-fibre fraction were 15.6% and 35.7% respectively.

The separated top layer was then further diluted with water (1 part to 5 parts water), stirred and then excess protein removed centrifugally. The cleaned material was then spray dried to a light-cream coloured powder.

The dried top layer was further analysed for β-glucan content, sugar, residual protein and oil etc with the following results:
β-glucan: 24.8%, protein: 5.3%, fat: 1.6%

A sub-sample of the dried top-layer material was then dissolved in 0.05 M sodium chloride solution to a concentration of 0.1% and the molecular weight of the polymeric components was estimated using HPSEC on a combined Ultragel GPC column system, using pullulans as Standards. The mean peak molecular weight of the β-glucan component of the material was estimated at >1.3 million Daltons.

Example 4

A trial equivalent to that described in example 1 was performed with an extra two steps being added to the procedure. The separated top-layer was not immediately freeze-dried, but was diluted with water (1 part to 5 parts water) and excess residual protein was removed centrifugally. The resulting mix was then passed through an Ultra Filter containing a 0.1 µm membrane, to remove lower molecular weight components, i.e., sugars such as maltodextrins and glucose. The retentate was then collected and freeze-dried. Analysis of the dried fraction gave the following results showed a β-glucan content of 38.4% (dry matter basis), with 4.6% protein.

GPC analysis of the product after redissolving in 0.05 M sodium chloride solution, showed a β-glucan peak with mean molecular weight of 1,200,500 estimated against pullulan standards.

Example 5

Raw material was prepared as follows: Oat grain was first de-hulled and the de-hulled grains were dry milled and 50% by weight of the grain was retained as the coarser fraction. 575 g of this material was suspended in 4 liters of water at a temperature of 95° C., in a 5 liter reaction vessel fitted with a mechanical stirrer. α-amylase enzyme (35 units) was added to the suspension and the mixture was incubated, with stirring and intermittent wet-milling, for 1 hour. After this time, the pH was dropped to 5.3, the temperature lowered to 65° C. and pullulanase enzyme was added (35 units), the mixture being incubated for 30 minutes with stirring. Enzymes were then completely de-activated by heating of the suspension in an autoclave at 140° C. for some minutes.

The resulting suspension was then centrifuged, producing four distinct layers which were separated and collected: a viscous top layer rich in soluble dietary fibre, particularly β-glucan, an aqueous layer, a protein-oil rich layer and a bottom layer containing the insoluble fibrous part of the milled oat. The top-layer and protein-oil layers were freeze dried prior to analysis. The fibrous layer was dried at 60° C. in an oven.

The yields of top layer, protein-oil fraction and the fibre fraction were 10.3%, 15.1% and 15.6% respectively, on a dry matter basis.

The top layer was further analysed for β-glucan content, residual protein and oil etc with the following results:
β-glucan: 18.2%, protein: 3.9%, fat: 0.1%

A sub-sample of the dried top-layer material was then dissolved in 0.05 M sodium chloride solution to a concentration of 0.1% and the molecular weight of the polymeric components was estimated using HPSEC on a combined Ultragel GPC column system, using pullulans as Standards. The mean molecular weight of the β-glucan component of the material was estimated at >1.3 million Daltons.

Example 6

The top layer isolated from oat in example 1 was further treated using an amyloglucosidase enzyme preparation which was cleaned of β-glucanase side activity as follows: 2 ml of AMG was firstly passed through a column containing anion exchange resin (Bio-Rad AG 1-X4) equilibrated in 25 mM phosphate buffer, pH 5.8 Bound protein was then eluted from the column by application of a linear sodium chloride gradient, from 0 to 1 M. The major protein band was collected and re-concentrated to 2 ml using a 1000 Dalton ultrafilter. The partially cleaned enzyme was then passed onto a column containing hydrophobic interaction chromatography support material (Blo-Rad Macro-Prep t-Butyl HIC Support), equilibrated using 50 mM phosphate buffer, pH 6.0, containing 1.5 M ammonium sulphate. Bound enzyme was then eluted from the column by application of a linear decreasing gradient of ammonium sulphate from 1.5 M to 0. The major protein band eluting from the column was collected, concentrated to 2 ml using a 1000 Dalton ultrafilter and then utilised as cleaned AMG as described below.

100 ml of the top layer containing 24.5% β-glucan (on a dry matter basis) and total 6% dry matter, was diluted to 200 ml with deionised water in a Pyrex® beaker, pH being adjusted to 4.6. The sample was placed in a water bath at 60° C., with magnetic stirring, and 100 µl of the cleaned AMG was added to the mix. Incubation was carried out for two hours, after which time the sample was heated to 120° C. in an autoclave, to deactivate the enzyme.

A sub-sample (0.5 ml) was removed from the vessel and was analysed using GPC for the molecular weight distribution of dissolved components, as described in example 1 above. The mean molecular weight of the β-glucan component of the material was measured at >1.3 million Daltons. A peak due to higher molecular weight dextrins encountered in the GPC profile of the product from example 1 had disappeared and a new peak at very low molecular weight was noted, due to dextrin hydrolysis.

The remainder of the sample was precipitated into a 1:1 mix of water and ethanol (500 ml) and the β-glucan was observed to precipitate in "strings" which were readily filtered from the liquid. These were then centrifuged to remove excess liquor and the white pellets were freeze dried, resulting in a cream powder.

Analysis of the product gave the following compositional results: β-glucan 62.8%, protein 4.2%, fat 0.1%. The remainder was mainly maltose, maltotriose and glucose.

A further GPC analysis was then performed on the dried product, after redissolving in 0.05 M sodium chloride solution. This yielded equivalent results, in terms of the mean peak molecular weight of the β-glucan component of the product, compared to the analysis carried out before drying.

Example 7

A procedure equivalent to that described in example 6 was performed, using the same raw material. However, instead of the hydrolysis product being precipitated after the 2 hour incubation, the liquor was ultra-filtered through an 0.1 μm membrane, the retentate being subsequently freeze dried.

Analysis of the product gave the following compositional results: β-glucan 44.6%, protein 4.3%, fat 0.4%. The remainder was mainly maltose, maltotriose and glucose.

GPC analysis of the product after redissolving in 0.05 M sodium chloride solution, showed a β-glucan peak with mean molecular weight of 1,130,500 estimated against pullulan standards.

Example 8

A procedure equivalent in most respects to that described in example 6 was performed, using the same raw material, with the further addition of a xylanase enzyme preparation (50 μl) to the solution 15 minutes before the end of the incubation period (ie after 105 minutes).

After enzyme inactivation (autoclaving at 120° C.), the sample was precipitated into a 1:1 mix of water and ethanol (500 ml) and the β-glucan was observed to precipitate in "strings" which were readily filtered from the liquid. These were then centrifuged to remove excess liquor and the white pellets were freeze dried, resulting in a cream powder.

Analysis of the product gave the following compositional results: β-glucan 64.4%, protein 4.0%, fat 0.2%. The remainder was mainly maltose, maltotriose and glucose.

GPC analysis of the product after redissolving in 0.05 M sodium chloride solution, showed a β-glucan peak with mean molecular weight of 810,600 estimated against pullulan standards.

Example 9

In order to evaluate the quality of the β-glucans formed in the procedure disclosed in U.S. Pat. No. 6,592,914B1 and WO 00/24270 to Triantafyllon, a comparison experiment was run according to the method disclosed in the Example of Triantafyllon. Oat bran obtained from the milling of heat-treated oat grain containing 6.4% β-glucan, as determined by the McLeery method, was used in the experiment 50 g of this sample was slowly added to a beaker placed in a thermostatted water-bath, which contained 360 g of delonised water, 0.5 g of β-amylase enzyme (obtained from Genencor), preheated to 55° C. The mixture was constantly stirred using an overhead mechanical stirrer fitted with a "propeller" mixer during addition of the oat bran, which took ten minutes. The beaker and contents were then kept in the 55° C. water bath for 2 hours with continued mechanical stirring. After this time, the beaker was transferred to a boiling water bath for fifteen minutes in order to deactivate the enzyme.

The entire contents of the beaker were then decanted into a centrifuge flask and the material was allowed to cool and was then centrifuged at 5000 rpm for 10 minutes. Fibrous solids and a grayish protein layer clearly separated at the bottom of the tube from a single layer aqueous supernatant containing the soluble and solubilised components of the treated oat meal. No viscous top-layer, distinct from a second aqueous layer, was observed.

The aqueous phase was decanted from the solids and analysed. After careful freeze drying, 16.1 g of a cream to light brown powder was obtained which contained about 1.5 g of β-glucan as determined using the Mcleery enzymatic method. This represents a β-glucan content of between 9 and 10% in the separated dry solid.

Both the dry solid and a small subsample of the supernatant retained before drying, were analysed using HPSEC (High Performance Size Exclusion Chromatography) on a combined Ultragel GPC column system, using pullulans as Standards. No high molecular weight peak above 200,000 Daltons was observed in either sample, indicating that the native β-glucans in the meal had been degraded during the treatment. This is presumed the major reason a distinct viscous, β-glucan rich top-layer was not observed. For such a phenomenon, the β-glucan component that is solubilised must be maintained at molecular weights of at least 1-1.5 million Daltons.

Example 10

A further experiment was run, which was exactly as described above in Example 9 except that a pullulan enzyme, 0.2 g, (obtained from Novo Nordisk) was added along with the β-amylase.

Very similar results were obtained and again, no distinct viscous top-layer was observed to separate. GPC analysis confirmed the absence of a particularly high molecular weight peak for β-glucan.

Example 11

A final experiment was then run. 5 g of the β-glucan rich powder produced as described in example 1, which contained 24.5% β-glucan with a measured peak molecular weight of greater than 1.3 million Daltons, was dissolved in 50 g of delonised water in a beaker which was placed in a water bath thermostatted at 55° C. A viscous solution formed. 0.1 g of the same β-amylase enzyme supplied by Genencor (Example 9) was added to the mixture, which was then gently magnetically stirred for 2 hours at 55° C. The viscosity of the solution was noted to drop considerably, and a sub-sample was removed at 2 hours for HPSEC analysis using the system described above. The β-glucan peak at high molecular weight had disappeared and a new, low molecular weight peak (less than 150,000 Daltons) appeared in the chromatogram. This strongly indicates that the enzyme treatment used degrades the β-glucan molecule, probably due to a side-activity within the preparation. Such a degradation occurring during processing of an oat meal would of course crucially prevent the formation of a distinct viscous top layer according to our observations.

Thus the comparative examples show that a separate phase comprising an increased amount of β-glucans will not be formed. The comparative examples show as well as that any β-glucan will have a very much smaller molecular-weight than the β-glucans isolated according to the present invention.

Thus the hydrolysate mixture of the U.S. Pat. No. 6,592,914 B1 and WO 00/24270 to Triantafyllon can not be used for the same purposes as the β-glucan fractions of the present invention.

FIGURE LEGENDS

Figure 2:
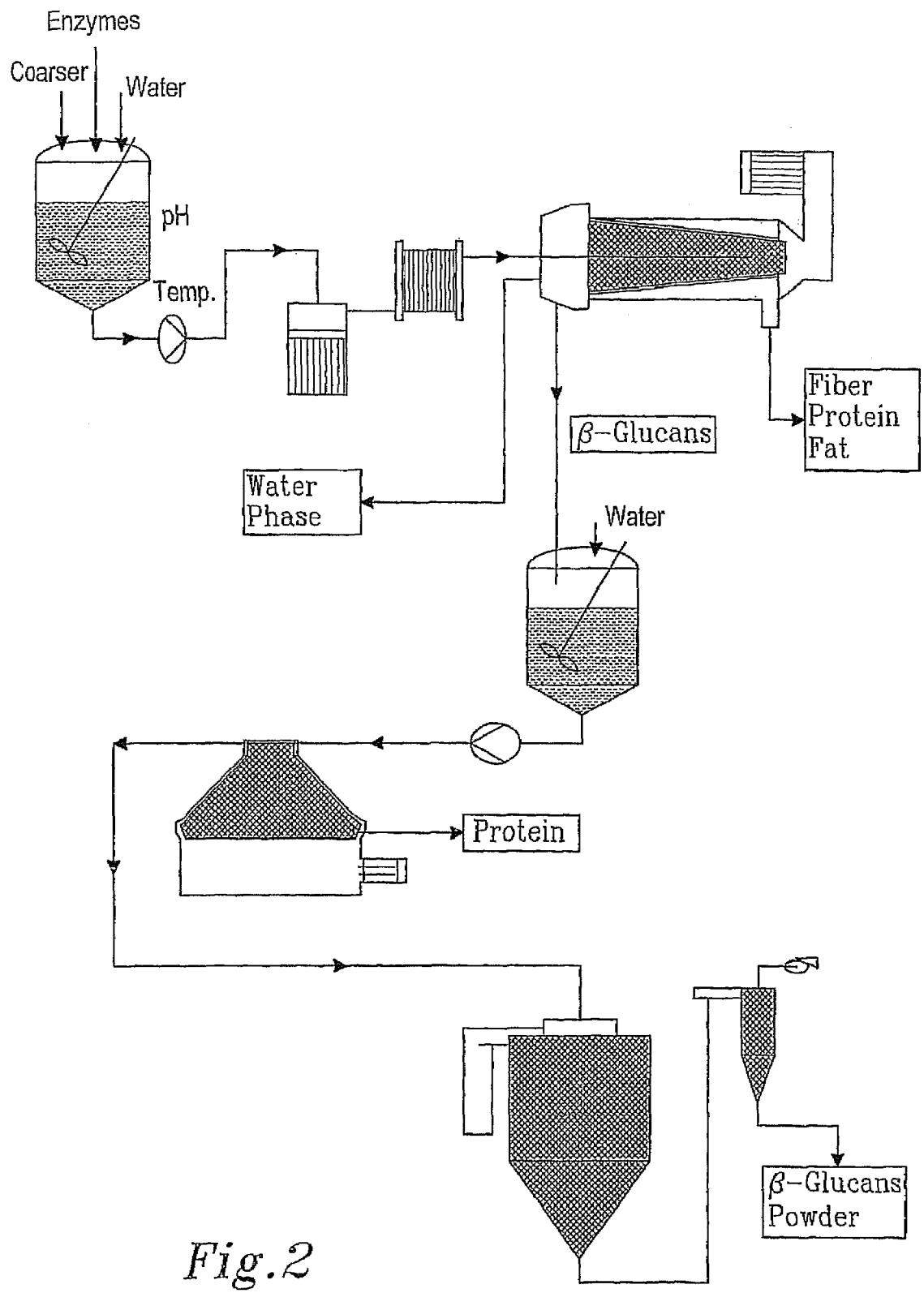

FIGS. 1 and 2 show a schematic overview of the set-up necessary for an industrial process wherein the set-up comprises two parts, viz, a dry process part and a wet process part.

The dry part (FIG. 1) consists of a bin 1 for storing oat or barley prior to use. The grains are transported via a transporting screw 2 to a cleansing means 10 and optionally dosing vessel 3 for weighing in off grains which are transferred to a dehulling apparatus 4, where hulls are taken off via separator 5. The dehulled grains are transferred, via a bin 6, to a mill comprising milling rolls and sieves, generally denoted 7, from where flour is retained in a bin 8, and coarser fraction is transferred to and retained in a bin 9 for further treatment.

The coarser fraction is now transferred to the wet part (FIG. 2) where it is introduced in a reaction vessel 11, together with the enzymes used and water to provide a slurry. pH control sensor (not shown) is applied to the reaction vessel as well as a heating jacket or other temperature controlling means (not shown). The reacted mixture is transferred via a wetmill 18 and a heat exchanger 12 to a separator 13 in the form of a decanter, where the top fraction/layer is transferred to a further reaction vessel 14, where the top layer is mixed with water to wash the product by separating of any entrapped protein being removed in a decanter 15, whereupon the β-glucan fraction is evaporated to produce a β-glucan powder in driers 16 and 17. An intermediate layer is removed as a water phase 19, and a layer comprising solids in the form of fibres, protein and fat is removed as a solids layer 20.

The invention claimed is:

1. A process for extraction of soluble dietary fibre complex from oat and barley grains using an enzymatic hydrolysis treatment,
    wherein
    non-heat treated grain is milled and endosperm depleted fractions thereof being rich in β-glucans are recombined, without any further heat treatment; and
    dispersed in water; and
    subjected to enzymatic treatment with starch degrading enzymes in a sequence utilizing first α-amylase and then amyloglucosidase enzyme, said starch degrading enzymes being substantially cleaned of β-glucanase side activity, said endosperm depleted fractions, water and starch degrading enzymes forming a hydrolysate mixture,
    said enzymatic treatment is followed by an optional step of enzyme inactivation by wet heat treatment,
    whereby the hydrolysate mixture forming spontaneously at least one viscous, aqueous top layer upon a second aqueous layer, is subjected to a separation process to isolate said at least one viscous, aqueous top layer comprising soluble dietary fibre complex, containing more than 20% β-glucan on a dry matter basis.

2. A process according to claim 1, wherein a second aqueous fraction layer substantially free of β-glucans, and at least a third fraction layer comprising protein and oil together with insoluble fibrous material from the milled grain are isolated.

3. A process according to claim 1, wherein the β-glucan has a molecular weight of at least 400,000 Daltons.

4. A process according to claim 1, wherein the β-glucan has a molecular weight of at least 800,000 Daltons.

5. A process according to claim 1, wherein the β-glucan has a molecular weight of at least 1,300,000 Daltons.

6. A process according to claim 1
    wherein the milled cereal grain is treated with starch degrading enzymes in a sequence utilizing first α-amylase and then amyloglucosidase enzyme being free of β-glucanase side activity.

7. A process according to claim 1,
    wherein the milled cereal grain is treated with starch degrading enzymes in a sequence utilizing first α-amylase and then amyloglucosidase enzyme being free of β-glucanase side activity, in which the amyloglucosidase enzyme is used for 40 minutes or less, at a temperature exceeding 55° C.

8. A process according to claim 1,
    wherein amyloglucosidase enzyme is substantially cleaned of β-glucanase side activities prior to use, in a two step procedure using anion exchange followed by hydrophobic interaction chromatography, a major protein band eluting from the hydrophobic interaction chromatography column being utilized as the cleaned enzyme.

9. A process according to claim 1,
    wherein the separated top-layer rich in soluble dietary fibre is further treated in a wet state, after optionally further diluting with water, with one or a combination of more than one of the following enzymes of the type: xylanases, amyloglucosidases, pullulanases, cellulases.

10. A process according to claim 1,
    wherein the top-layer rich in soluble dietary fibre is further treated in a wet state, after optionally further diluting with water, with amyloglucosidase enzyme, in which the amyloglucosidase enzyme is substantially cleaned of β-glucanase side activities prior to use, in a two step procedure using anion exchange followed by hydrophobic interaction chromatography, a major protein band eluting from the hydrophobic interaction chromatography column being utilized as the cleaned enzyme.

11. A process according to claim 1, wherein the β-glucan is dried.

* * * * *